United States Patent [19]

Schmidt

[11] 4,384,148
[45] May 17, 1983

[54] HYDRATION OF OLEFINS

[75] Inventor: Robert J. Schmidt, Rolling Meadows, Ill.

[73] Assignee: UOP Inc., Des Plaines, Ill.

[21] Appl. No.: 352,840

[22] Filed: Feb. 26, 1982

[51] Int. Cl.³ .................. C07C 29/04; C07C 29/10; C07C 27/02

[52] U.S. Cl. .................. 568/907; 568/671; 568/877

[58] Field of Search .................. 568/907, 877, 671

[56] References Cited

U.S. PATENT DOCUMENTS

| | | | |
|---|---|---|---|
| 1,894,479 | 1/1933 | Bader | 568/671 |
| 2,317,949 | 4/1943 | Burk | 568/877 |
| 2,373,359 | 4/1945 | Voogd et al. | 568/889 |
| 2,519,061 | 8/1950 | Mason | 568/907 |
| 2,533,808 | 12/1950 | Howlett et al. | 568/889 |

FOREIGN PATENT DOCUMENTS 2041364  9/1980  United Kingdom .................. 568/877

Primary Examiner—Joseph E. Evans
Attorney, Agent, or Firm—James R. Hoatson, Jr.; Raymond H. Nelson; William H. Page, II

[57] ABSTRACT

Alcohols may be obtained by the indirect hydration of olefinic hydrocarbons in which the olefinic hydrocarbon is esterified by treatment with an organic acid such as acetic acid. The organic esters may then be hydrolyzed by treatment with water to form hydrolysis products comprising alcohols and ethers which may be separated from the reconstituted organic acid. The alcohol products are then separated from the ether product, the latter which may then be further treated by thermal cracking, decomposition, or hydrolysis to form an additional amount of the desired alcohol.

13 Claims, 1 Drawing Figure

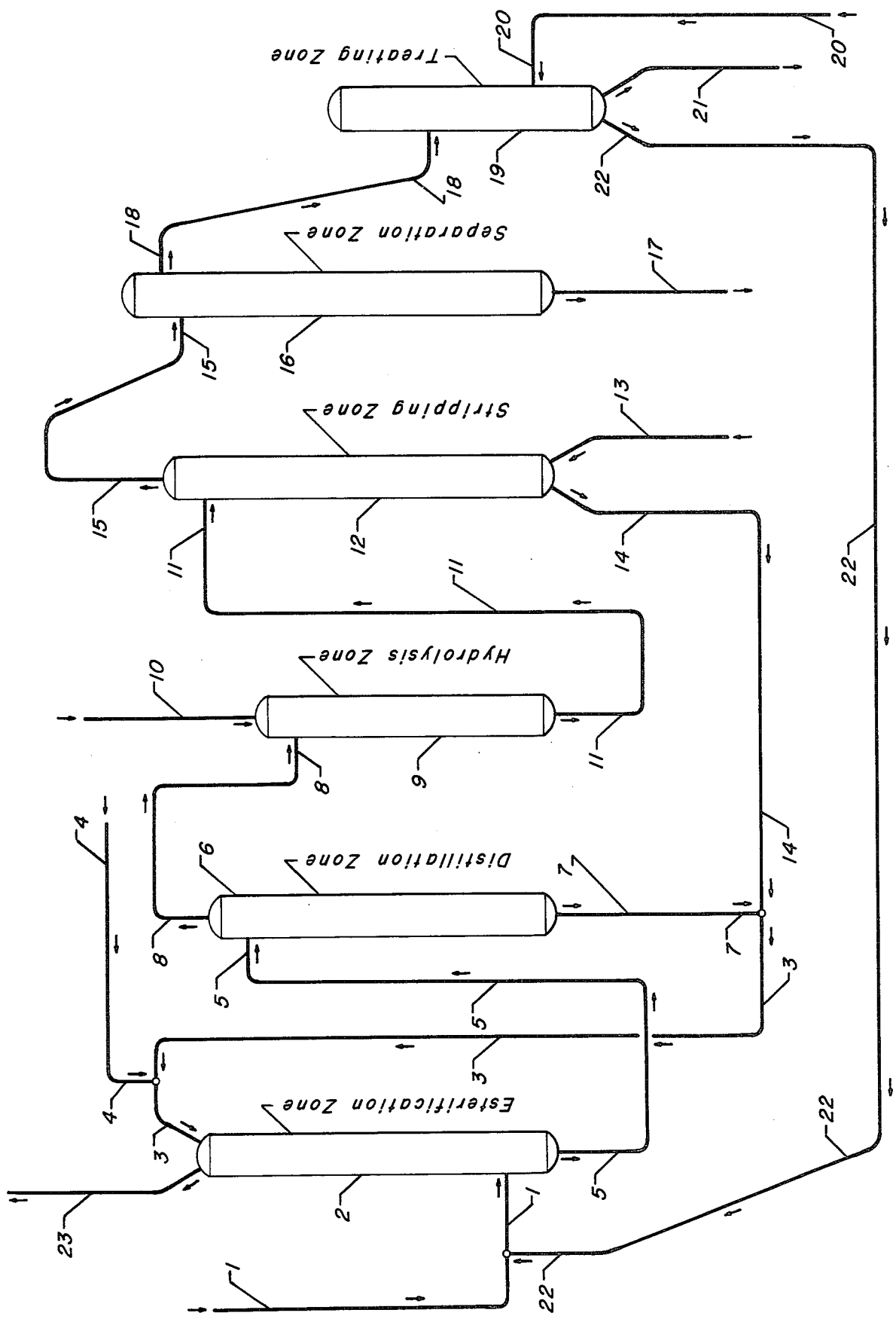

HYDRATION OF OLEFINS

BACKGROUND OF THE INVENTION

The indirect hydration of olefins to alcohols and ethers has employed, in the conventional process, sulfuric acid as the esterification agent to form dialkyl sulfate and alkyl hydrogen sulfate esters. However, in the conventional processes, it is necessary to effect a costly reconcentration or reconstitution of sulfuric acid, the reconcentration resulting from the hydrolysis of the esters with an excess of water in order to prepare the necessary alcohols. The use of alcohols in the chemical industry is well known and covers a wide variety of fields. For example, ethyl alcohol is a staple alcohol of commerce and is used as a solvent, as an intermediate in organic derivatives, of dyes, synthetic rugs, synthetic rubber, detergents, surface coatings, cosmetics, pharmaceuticals, explosives, beverages, etc. Likewise, propyl alcohol and especially isopropyl alcohol is used in the manufacture of acetone, as a solvent for essential and other oils, gums, resins, etc., deicing agent for liquid fuels, pharmaceuticals, perfumes, lacquers, etc., while butyl alcohol is used as a solvent in varnish, lacquers, etc. In addition, other alcohols may be used as a component in fuels such as gasoline, etc.

As will hereinafter be shown in greater detail, it has now been discovered that an olefinic hydrocarbon may be hydrolized to form an alcohol as well as an ether by utilizing an organic acid as an esterification agent, thereby eliminating the requirement of reconcentrating the acids which are utilized as the aforesaid esterification agent.

SUMMARY OF THE INVENTION

This invention relates to a process for the indirect hydration of an olefinic hydrocarbon to form an alcohol and an ether. More specifically, the invention is concerned with a process for the indirect hydration of an olefinic hydrocarbon to an alcohol and an ether using an organic acid as the esterification agent.

As will be shown in greater detail, by utilizing the process conditions and flow scheme of the present process, it has now been discovered that an indirect hydration of an olefinic hydrocarbon to form a desired product may be accomplished in a commercially attractive and economical manner, thus obviating the need for relatively costly equipment and process modification.

It is therefore an object of this invention to provide a process for the indirect hydration of an olefinic hydrocarbon while avoiding the addition of an excess amount of hydrating agent.

A further object of this invention is to provide a process for obtaining alcohols from olefinic hydrocarbons while avoiding the necessity for reconcentrating the esterification agent utilized in said process.

In one aspect, an embodiment of this invention is found in a process for the hydration of an olefinic hydrocarbon which comprises esterifying said olefinic hydrocarbon with an organic acid at esterifing conditions in an esterification zone, hydrolyzing said organic ester with water at hydration conditions in a hydration zone, stripping the resultant alcohol and ether hydrolysis products from the reconstituted organic acid, separating and recovering said alcohol from said ether at separaton conditions in a separation zone, treating said ether at treatment conditions in a treatment zone to produce an additional amount of said alcohol, and recovering said alcohol.

A specific embodiment of this invention is found in a process for the hydration of ethylene which comprises esterifying said ethylene with acetic acid at a temperature in the range of from about 50° to about 150° C. and a pressure in the range of from about 200 to about 1500 psi, hydrolyzing the resultant ethyl acetate by treatment with water at a temperature in the range of from about ambient to about 200° C. and a pressure in the range of from about atmospheric to about 1500 psi, stripping the resultant ethyl alcohol and diethyl ether from the reconstituted acetic acid, utilizing a stripping gas comprised of nitrogen at a temperature in the range of from about ambient to about 200° C. and a pressure in the range of from about atmospheric to about 1500 psi, separating said ethyl alcohol and said diethyl ether at a temperature in the range of from about ambient to about 200° C. and a pressure of from about subatmospheric to about 150 psi and recovering said ethyl alcohol, treating said diethyl ether by hydrolysis with water at a temperature in the range of from about 150° to about 250° C. and a pressure in the range of from about subatmospheric to about 1500 psi to produce an additional amount of ethyl alcohol and ethylene, and recovering the desired alcohol.

Other objects and embodiments will be found in the following further description of the invention.

DESCRIPTION OF THE INVENTION

As hereinbefore set forth, the present invention is concerned with a process for the indirect hydration of olefinic hydrocarbons to form the corresponding alcohol and ether utilizing a process which includes an esterification step in which the esterification agent comprises an organic acid. The esterification is followed by a hydrolysis step in which the organic ester is treated with water in a stoichiometric amount, thus eliminating the need for a reconcentration of the acids employed and requiring only a reconstitution of the acid which may then be recycled to the esterification zone for further use as the desired esterification agent with the concomitant elimination of added equipment and expenditure of energy as well as the reduction in the overall cost of the process.

The process described herein involves the utilization of a dilute olefinic hydrocarbon feedstock such as off-gases resulting from a prior refining or reforming operation. The olefins may be preset as a mixture of gases containing from 2 to about 4 carbon atoms or more in the chain, specific examples of these olefinic hydrocarbons being ethylene, propylene, butylene, etc. It is also contemplated within the scope of this invention that olefinic hydrocarbons containing more than 5 carbon atoms such as the isomeric amylenes, hexenes, heptenes, octenes, nonenes, decenes, etc. may also be utilized as feedstocks for the preparation of alcohols and ethers.

As an example of the process, the feedstock is charged to an esterification zone wherein it is contacted with an organic acid. Some specific examples of organic acids which may be employed as the esterification agent will include fatty acids, preferably of a relatively low molecular weight such as formic acid, acetic acid, propionic acid, butyric acid; chloro-substituted fatty acids such as chloroacetic acid, bromoacetic acid, fluoroacetic acid, trichloroacetic acid, tribromoacetic acid, trifluoroacetic acid, chloropropionic acid, bromopropionic acid, fluoropropionic acid; the isomeric chloro-, bromo- , fluoro-, dichloro-, difluoro-, dibromobutyric acids, etc. It is to be understood that these acids are merely representative of the class of organic acids which may be employed to effect the esterification reaction to produce an organic ester, and that the present invention is not necesarily limited thereto. The esterification conditions which are employed to effect the desired reaction will include a temperature in the range of from about 50° to about 150° C. and a pressure in the range of from about 200 to about 1500 psi. After allowing the esterification process to proceed for a predetermined period of time, the resultant organic esters are withdrawn from the trans-esterification zone and passed to a hydrolysis zone.

In the hydrolysis zone which is maintained at hydrolysis conditions including a temperature range of from ambient (20°–25° C.) up to about 200° C. or more and a pressure ranging from atmospheric to about 1500 psi, the organic esters are converted to the corresponding alcohols and ethers by treatment with water, while the organic acid is reconstituted. The mixture of alcohols and ethers and reconstituted acids is then withdrawn from this hydrolysis zone and passed to a stripping zone wherein the mixture is contacted with a stripping agent which may comprise a stripping gas such as nitrogen utilizing stripping conditions which will include a temperature in the range of from about ambient to about 200° C. and a pressure in the range of from about atmospheric to about 1500 psi. Following this, the stripped alcohols and ethers are withdrawn from the stripping zone and passed to a separation zone while the reconstituted organic acid is recycled back to the esterification zone.

In the separation zone, the alcohols and ethers are separated by conventional means such as distillation, while employing separation conditions which again will include temperatures in the range of from about ambient to about 200° C. utilizing pressures which may range from about subatmospheric (1 psia) to about 150 psi. The alcohol which is separated from the ether is recovered while the latter may then be further treated in a treating zone whereby the ether is converted to the desired alcohol and olefinic hydrocarbon, the latter being recycled to the esterification zone. The treatment of the ether to form the desired alcohol may be effected in either a thermal manner or by hydrolysis. The thermal treatment of the ether to form the alcohol will be effected at treating conditions which will include a temperature in the range of from about 500° to about 750° C. while employing a pressure in the range of from about subatmospheric to about 1500 psi. It is contemplated that the thermal decomposition of the ether to the alcohol and olefinic hydrocarbon may be effected in the presence of an acidic type catalyst which will include such components as acidic resins; high surface area inorganic oxides such as alumina, silica-alumina, etc; zeolites; etc. When utilizing a hydrolsis treatment to form the desired alcohol, the ether will be treated with water at a temperature in the range of from about 150° to about 250° C. utilizing pressures similar to those hereinbefore set forth, that is, from about subatmospheric to about 1500 psi. The olefinic hydrocarbons which are obtained by the decomposition of the ether may then be used as feeds for other processes or, if so desired, may be recycled back to the esterification zone for further treatment with an organic acid of the type hereinbefore before set forth to form the aforementioned organic ester.

BRIEF DESCRIPTION OF THE DRAWING

The present process will be further illustrated with reference to the accompanying FIGURE which illustrates a simplified flow diagram of the inventive feature of the present process.

Various valves, coolers, condensers, pumps, heaters, controllers, etc. have been eliminated as not being essential to the complete understanding of the present invention. However, the illustration of these, as well as other essential appurtenances will become obvious as the drawing is described.

Referring now to the FIGURE, a feedstock such as an off-gas obtained from a reforming operation containing dilute olefinic hydrocarbons or a feedstock containing pure olefinic hydrocarbons is charged through line 1 to an esterification zone 2. In esterification zone 2, the feedstock is contacted with an organic acid of the type hereinbefore set forth which is charged to zone 2 through line 3. The amount of organic acid which is used to effect the esterification of the olefinic hydrocarbon to form an organic ester is predetermined, and may require the addition of some make-up acid which is charged through line 4 and 3 to zone 2. In esterification zone 2, the organic ester is formed and after a predetermined period of time, the organic ester and any unreacted organic acid is withdrawn from zone 2 through line 5 and passed to a distillation zone 6. Any feed gas which remains from the esterification reaction is discharged from zone 2 through line 23 and may, of so desired, be used as a fuel to form liquid petroleum gas, etc. In distillation zone 6, any unreacted organic acid is separated from the organic ester and withdrawn through line 7 for recycle back to esterification zone 2 through line 3.

The organic ester which has been separated from the organic acid is withdrawn from distillation zone 6 through line 8 and passed to hydrolysis zone 9. In hydrolysis zone 9 which is maintained at hydrolysis conditions which include a temperature in the range of from about ambient to about 200° C. and a pressure ranging from atmospheric to about 1500 psi, the organic ester is contacted with a stoichiometric amount of water which is added to zone 9 through line 10. After hydrolysis of the organic ester, the reaction mixture comprising the reconstituted organic acid and the hydrolysis product containing a mixture of alcohol and ether is withdrawn from zone 9 through line 11 and passed to a stripping zone 12. In stripping zone 12, the reaction mixture is subjected to the action of a stripping agent which may comprise a gas such as nitrogen, said gas being charged to zone 12 through line 13. Alternatively, if so desired, the stripping zone may comprise a distillation unit in the event that the use of external stripping means such as the gas is not contemplated. The reconstituted organic acid is withdrawn from zone 12 through line 14 for recycle by means of line 3 back to esterification zone 2. The hydrolysis product comprising a mixture of alcohol and ether is withdrawn from stripping zone 12 through line 15 and passed to a separation zone 16.

In separation zone 16, which is maintained at a temperature in the range of from about ambient to about 200° C. and a pressure which may range from subatmospheric (1 psia) up to about 150 psi, the desired alcohol product is separated from the dialkyl ether and withdrawn from separation zone 16 through line 17 where it is passed to storage. The dialkyl ether which is separated from the alcohol is withdrawn from separation zone 16 through line 18 and passed to treatment zone 19.

In treatment zone 19, the dialkyl ether may be treated in either a thermal decomposition manner at temperatures which may range from about 500° C. up to about 750° C. to form the corresponding alcohol and olefinic hydrocarbon, or, alternatively, the ether may be subjected to hydrolysis by treatment with water which, in the event that such a treating system is used, will be charged to treatment zone 19 through line 20. In the event that the ether is subjected to hydrolysis, the hydrolysis conditions which are employed will include a temperature in the range of from about 150° to about 250° C. and a pressure in the range of from subatmospheric to about 1500 psi. The resulting alcohol is withdrawn from treatment zone 19 through line 21 and passed to storage while the olefinic hydrocarbons may be recycled back to esterification zone 2 through lines 22 and 1 for use as a portion of the feedstock in this reaction, or utilized as a feed for other processes.

By utilizing the present process, it is possible to operate the same at a maximum efficiency inasmuch as by treating the olefinic hydrocarbon with an organic acid followed by a subsequent hydrolysis employing a stoichiometric amount of water, it is possible to obviate the dilution of the acid with a concurrent avoidance of the necessity of reconcentrating said acid in order that it may be further utilized as an esterification agent. The elimination of this reconcentration step will greatly reduce the overall expense of the operation and thereby render the same more commercially attractive to operate.

The following examples are given for purposes of illustrating the process of this invention. However, it is to be understood that these examples are given merely for purposes of illustration and the the present process is not necessarily limited thereto.

EXAMPLE I

To illustrate the esterification reaction of the present process, 58.0 grams of acetic acid were placed in a 300 cc stainless steel stirred autoclave. A blend gas comprising 18.5% of ethylene and 81.5% of nitrogen was charged to the reactor until an initial operating pressure of 450 psig was reached. The autoclave was heated to a temperature of 80° C. and stirred at a rate of 560 rpm. The esterification reaction was allowed to proceed for a period of 60 minutes at the end of which time heating was discontinued and the autoclave was allowed to return to room temperature. The excess pressure was discharged, the autoclave was opened and an analysis of the reaction mixture determined that there had been a 20% conversion of ethylene to form ethyl acetate.

When the above experiment was repeated using as a catalyst 57.95 grams of acetic acid and 1.42 grams of silver acetate under similar conditions, there was obtained a 22% conversion of ethylene to ethyl acetate.

EXAMPLE II

The ethyl acetate which was obtained from the above example was subjected to distillation to separate ethyl acetate from any unreacted acetic acid, the distillation being effected at a temperature of 110° C. and a pressure of 760 mm of mercury for a period of 30 minutes. There was obtained from this distillation 68.5 mole % of ethyl acetate and 34.3 mole % of acetic acid.

EXAMPLE III

The ethyl acetate which was recovered from the above experiment was subjected to hydrolysis by placing a feedstock of water and ethyl acetate in a mole ratio of 5:1 water to ethyl acetate in an 850 cc rotating autoclave. The autoclave was heated to a temperature of 154° C. under a pressure of 85 psig and maintained thereat for a period of two hours. At the end of this time, heating was discontinued, the excess pressure was discharged, and the autoclave was opened. Analysis determined that there had been a 57.4% conversion of the ethyl acetate with an 89.2 wt. % recovery of the product comprising ethyl alcohol and diethyl ether.

EXAMPLE IV

The acetic acid which was formed during the hydrolysis of the ethyl acetate may be separated from the ethanol and diethyl ether by subjecting the mixture to a stripping operation utilizing nitrogen as a stripping gas. The stripping of the acetic acid may be effected at a temperature of 90° C. for a period of 0.5 hours following which the diethyl ether may be separated from the ethanol in a distillation apparatus by heating the apparatus to a temperature of about 140° C., passing the ethanol to storage and recovering the ether.

EXAMPLE V

The diethyl ether which is separated from the alcohol may then be converted to an additional amount of alcohol by subjecting the ether to a thermal cracking at temperatures ranging from 540° to 710° C. at atmospheric pressure over quartz chips. Alternatively, the diethyl ether may be treated in an autoclave for a period of 6 hours in the presence of a catalyst such as resins sold under the trade names Amberlite XE-365 or Amberlyst 15, or an acid catalyst such as 12-tungstophosphoric acid at a temperature of about 250° C. to form the desired ethanol.

EXAMPLE VI

In a manner similar to that set forth in the above examples, other olefins such as propylene and butylene may be esterified with other organic acids such as chloroacetic acid or propionic acid. The resultant organic esters may then be separated from unreacted acid, hydrolyzed by treatment with water under similar operating conditions to form isopropyl alcohol, diisopropyl ether or sec-butyl alcohol and di-sec-butyl ether respectively. After separating the reconstituted chloroacetic acid and propionic acid, the aforesaid alcohols and ethers may be recovered and/or the ethers treated to a thermal cracking or catalytic reaction to form additional amount of alcohol.

I claim is my invention:

1. A process for the hydration of an olefinic hydrocarbon which comprises:
   (a) esterifying said olefinic hydrocarbon with an organic acid at esterifying conditions in an esterification zone to form an organic ester;
   (b) hydrolyzing said organic ester with water at hydration conditions in a hydration zone to form an alcohol and ether hydrolysis product containing reconstituted organic acid;
   (c) stripping said alcohol and ether hydrolysis product from said reconstituted organic acid;
   (d) separating said alcohol from said ether at separation conditions in a separation zone and recovering said alcohol as a primary product stream of said process;

(e) thermally decomposing said ether of step (d) in a thermal decomposition zone at a temperature in the range of from about 500° C. to about 750° C. and a pressure in the range of from subatmospheric pressure to about 1500 psi to produce olefinic hydrocarbons and alcohol as a secondary product stream of said process; and (f) recovering both primary and secondary product alcohol streams.

2. The process as set forth in claim 1 in which said esterification conditions include a temperature in the range of from about 50° to about 150° C. and a pressure in the range of from about 200 to about 1500 pounds per square inch.

3. The process as set forth in claim 1 in which said hydration conditions include a temperature in the range of from about ambient to about 200° C. and a pressure in the range of from about subatmospheric to about 1500 pounds per square inch.

4. The process as set forth in claim 1 in which the stripping of said alcohol and ether hydrolysis products from said reconstituted organic acid is effected as a temperature in the range of from about ambient to about 200° C. and a pressure in the range of from about atmospheric to about 1500 pounds per square inch.

5. The process as set forth in claim 1 in which said separation conditions include a temperature in the range of from about ambient to about 200° C. and a pressure in the range of from about subatmospheric to about 1500 pounds per square inch.

6. The process as set forth in claim 1 in which said stripping of said alcohol and said ether from said reconstituted organic acid is effected by treatment with a stripping gas.

7. The process as set forth in claim 6 in which said stripping gas is nitrogen.

8. The process as set forth in claim 1 which said organic acid is acetic acid.

9. The process as set forth in claim 1 in which said organic acid is chloroacetic acid.

10. The process as set forth in claim 1 in which said organic acid is propionic acid.

11. The process as set forth in claim 1 in which said olefinic hydrocarbon is ethylene, said alcohol is ethyl alcohol and said ether is diethyl ether.

12. The process as set forth in claim 1 in which said olefinic hydrocarbon is propylene, said alcohol is propyl alcohol, and said ether is dipropyl ether.

13. The process as set forth in claim 1 in which said olefinic hydrocarbon is butylene, said alcohol is sec-butyl alcohol, and said ether is di-sec-butyl ether.

* * * * *